United States Patent [19]

Sarfarazi

[11] Patent Number: 4,946,469
[45] Date of Patent: Aug. 7, 1990

[54] INTRAOCULAR LENS

[76] Inventor: Faezeh Sarfarazi, 25 Wiswall Rd., Newton Center, Mass. 02159

[21] Appl. No.: 340,925

[22] Filed: Apr. 20, 1989

[51] Int. Cl.$^5$ ............................................. A61F 2/16
[52] U.S. Cl. ...................................................... 623/6
[58] Field of Search ........................................... 623/6

[56] References Cited

U.S. PATENT DOCUMENTS 4,424,597 1/1984 Schlegel .................................. 623/6
4,664,666 5/1987 Barrett .................................... 623/6

FOREIGN PATENT DOCUMENTS 2124500A 2/1984 United Kingdom ..................... 623/6
2151371A 7/1985 United Kingdom ..................... 623/6

Primary Examiner—Ronald Frinks
Attorney, Agent, or Firm—Amster, Rothstein & Ebenstein

[57] ABSTRACT

An improved intraocular lens is provided which has a central optical portion formed of, for example, PMMA, and a soft, flexible supporting portion extending radially therefrom to support the intraocular lens in the evacuated posterior capsule of a human eye. The supporting portion is shaped to be compatible with the shape of the evacuated posterior capsule, and its outer periphery is rounded to softly fit into and be supported by the capsule without any pressure points.

10 Claims, 2 Drawing Sheets

INTRAOCULAR LENS

This invention concerns an improvement in intraocular lenses for implant into the human eye and particularly a lens to be implanted in the posterior chamber of the eye and within the posterior capsule of the natural lens after the nucleus of the lens has been removed.

Modern opthalmic surgical techniques have developed a number of devices and modalities for providing substitutions for the natural eye lens. Although significant advances have been made, current devices and techniques leave much to be desired.

Typical intraocular lenses in use today utilize an optical element which is supported by a pair of haptics to position the lens within the eye. The materials chosen for use are those which have been found to be tolerated by the patient and which do not deteriorate in that environment. Typically, the optical elements themselves are formed of PMMA (polymethyl methacrylate), and the haptic portions or support elements are formed of PMMA or metal elements which are not harmful to the eye. The implantation of these devices in the extremely small and extremely delicate environment of the eye has been beset with difficulties and problems, and the use of haptic members has produced a series of problems. Since it is required to insert the lens through the iris of the eye, it was believed that haptic support elements must extend in opposite directions from the lens such that it may be inserted axially through the iris and then rotated to allow the haptics to position the lens on two opposing sides. It has been found that too often lenses of that type thus installed migrate, and/or the haptic devices produce an adverse pathology at the small points where they contact the inner elements of the eye. Lenses with such support devices are shown, for example, in U.S. Pat. Nos. Re. 31640 and 4,588,406. Other types of implants have been suggested, such as in U.S. Pat. No. 4,254,509, for an interior lens to be placed in front of the iris, and in U.S. Pat. No. 4,172,297 which shows a lens intended to be held in position by attachment to the iris of the eye. U.S. Pat. No. 3,711,870 shows a lens designed to be sutured to the ciliary muscle of the eye, which lens has not been successful, presumably because it is too big to be practically inserted within the eye and because suturing to the ciliary muscle appears to be impractical. Reference to these patents and to the references cited therein provide much information as to the investigations and proposals which have been made in this area.

A need exists for an intraocular lens which has support means allowing the lens to be held within the natural lens capsule (after the nucleus has been removed) in a manner in which the lens is maintained on axis in the eye and where those support materials do not irritate or otherwise damage the eye. The inventor conceived that such support would be best provided by a soft and generally circular rim of support means which extends radially away from the optical portion of the lens, in all directions, to provide peripheral support completely around the entire periphery of the device where it physically contacts the interior portions of the eye. At the same time, such a lens must be capable of being inserted through the opening of the iris of the eye (which typically cannot be dilated greater than approximately 10 mm) and, alternatively, should be insertable through a slit in the anterior capsule of the natural lens which may be as small as 4.5 to 5 mm or smaller. The foldable lens disclosed and claimed herein meets each of those specifications.

Generally, it is an object of the present invention that there be provided an improved intraocular lens for insertion into a human eye in substitution for the natural lens which improves over such lenses heretofore available.

It is a more particular object of the present invention to provide such a lens which has means to hold that lens in position on axis within the eye by means which do not cause irritation or other harm to the eye and which may be inserted into the eye through an opening of dimensions much smaller than that of the lens itself.

In accordance with one preferred embodiment of the invention, there is provided an intraocular lens which is formed of a central portion of optical grade materials (for example, PMMA) and a soft peripheral flange portion extending radially outward from the central optical portion and shaped into a soft, flexible and three-dimensionally curved shape such that it both softly and securely positions the lens for support within the eye. The structure permits the entire lens to be folded for insertion into the eye through the small opening of the iris and a still smaller opening in the anterior capsule of the natural lens. Once inserted, the lens unfolds and is positioned in proper location. The intraocular lens may be formed of one material, or it may be formed of a first material for the central optical portion and another softer material for the surrounding supporting structure. For example, the optical portion may be of PMMA and the flange material may be of a soft flexible material such as a silicone or a hydrogel. It is contemplated that the lens in accordance with the present invention will find its best application when positioned within the natural lens capsule of the eye after an opening is formed in the anterior capsule and the nucleus of the natural lens is completely removed.

The above brief outline and description of the invention will be best appreciated by reference to the following description, in conjunction with the drawings, wherein.

Figure 1:
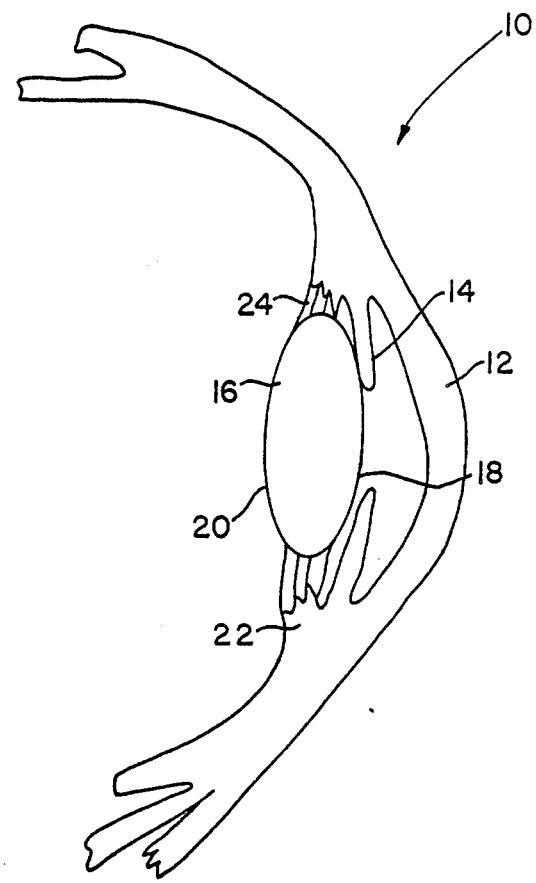
FIG. 1 is a partially schematic sectional view of a normal human eye.

FIG. 1 shows a simplified view of the forward portion of the human eye 10 including the cornea 12, the iris 14, the natural lens 16, the anterior capsule of the lens 18, and the posterior capsule 20. Surrounding the lens 16 is the ciliary body or ciliary muscles 22 which interconnect with the natural lens 16 by means of the zonule of Zinn which are schematically illustrated by the thin lings designated 24. The vitreous body fills the cavity 26. The retina lines the rearward portion of the cavity 26 and, of course, the optic nerve not visible in these drawings connects with the retina at the rear of that cavity.

At an earlier point in the history of lens implants, the entire natural lens was removed from the eye (the intracapsular technique) and an intraocular lens, for example, of the type shown in U.S. Pat. No. 4,588,406, was inserted with the haptic elements positioned at opposed points along the groove formed between the iris and the ciliary sulcus. Current practice is significantly advanced over that procedure. Today, the preferred procedure is to form an opening in the anterior capsule of the lens and remove the entire nucleus, leaving only the capsule (or bag) itself. The opening in the anterior capsule may be made by removing a disk-shaped portion of the anterior capsule of approximately 8 mm in diameter. Alternatively, a thin slit is made in the anterior capsule through which the nucleus of the lens is removed. The intraocular lens implant is then placed through the opening in the anterior capsule and positioned within the capsule, again by means of the haptic elements in the traditional lenses of the type referred to above. In those situations in which only a slit is formed in the anterior capsule, a full disk-like opening must be created before the intraocular lenses in current use can be implanted. It is in this environment that the intraocular lens of the present invention is intended to be utilized.

Figure 4:
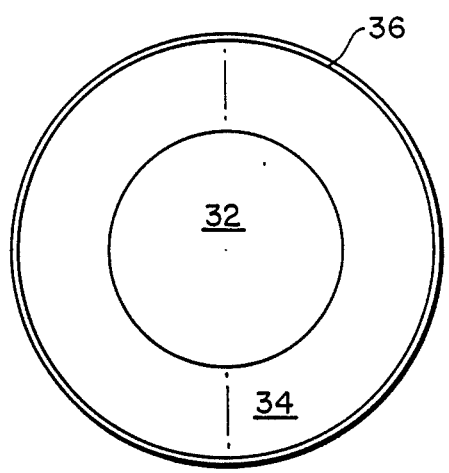
FIG. 4 is a plan view of an intraocular lens in accordance with the present invention.
Figure 5A:
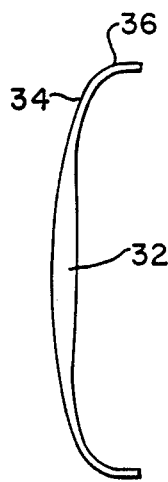
FIGS. 5A, B and C are sectional views of lenses in accordance with the present invention showing three alternative structures.
Figure 5B:
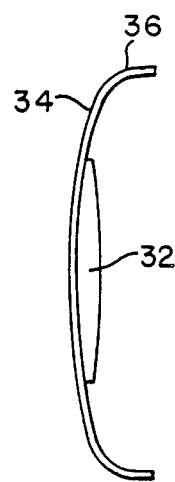
Figure 5C:
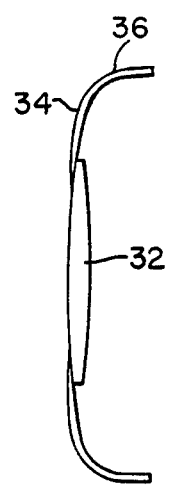

The intraocular lens 30 in accordance with the present invention is shown in plan view in FIG. 4 and in sectional views in FIGS. 5A, 5B and 5C. It should be understood that FIGS. 5A, 5B and 5C are vastly out of scale relative to the thickness of the lens. The lens is very thin, on the order of magnitude of tenths of millimeters and, therefore, cannot be illustrated in these drawings in anything even approaching the proper scale. Typically, the thickness of the outer region may be as small as approximately 0.25 mm, but the central portion will be thicker.

The lens 30 consists of a central ocular portion 32 which is the primary corrective portion of the lens. The central portion is typically biconvex and is about 4.5 mm in diameter (it may vary in diameter in a range from about 3 mm to about 7 mm). Surrounding the central ocular portion 32 is a generally dish-shaped supporting portion 34 and which is typically about 9.5 mm in outside diameter (and which also may have corrective optical characteristics). While the overall diameter of the outer supporting portion 34 is typically about 9.5 mm, it may vary in dimension, depending upon the size of the posterior capsule, and would generally be in the range of about 9 mm to about 14 mm. The entire lens 30 may be formed of a homogeneous material or, as in the presently preferred embodiment, the central optical portion 32 may be formed of PMMA and the outer supporting structure may be formed of silicone, a hydrogel or other materials as are widely known and used in soft contact lenses. These materials are well established as not being harmful to the eye and not subject to degradation within the eye.

The central optical portion 32 is formed with the proper optical properties for the particular patient in a manner known in the art and is relatively rigid. The outer soft supporting portion 34 is relatively thin compared to the optical portion 32 and is therefore flexible and soft as compared to the central portion. It provides gentle contact with the interior of the posterior capsule of the natural lens to thereby provide gentle support for the lens 30 in the eye. The overall shape of the lens 30 should conform to the natural shape of the patient's lens capsule (see FIGS. 2, 3, 5A, 5B and 5C). The periphery 36 of the lens 30 has a rounded shape adapted to conform to the natural shape of the outer portion of the eye capsule.

Future research may show that it will be possible to place the lens 30 at other locations in the eye. For example, in patients whose lens capsule cannot be used, it may be shows that the lens 30 can be positioned in the anterior chamber, between the iris and the cornea.

FIG. 5A shows a form of the lens in which the optical portion 32 is formed continuously with the outer portion 34. In FIG. 5B the optical portion 32 is shown on the inner surface of the lens 30, either formed on or mounted on the thin support portion 34; the optical portion could also be formed or mounted on the posterior face of the supporting portion 34. FIG. 5C shows a further variation in which the supporting portion 34 is secured to the optical portion 32 at or adjacent the outer edge of the optical portion. Each of these variations may be formed of homogeneous material, or two different materials, and may be formed, by molding or otherwise, at one time or by assembly.

Figure 2:
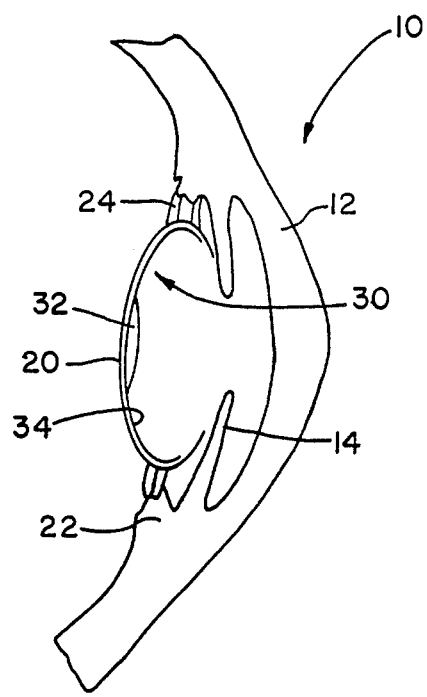
FIG. 2 is a sectional view, similar to FIG. 1, but with an intraocular lens in accordance with the present invention shown in position within the posterior capsule of the eye.
Figure 3:
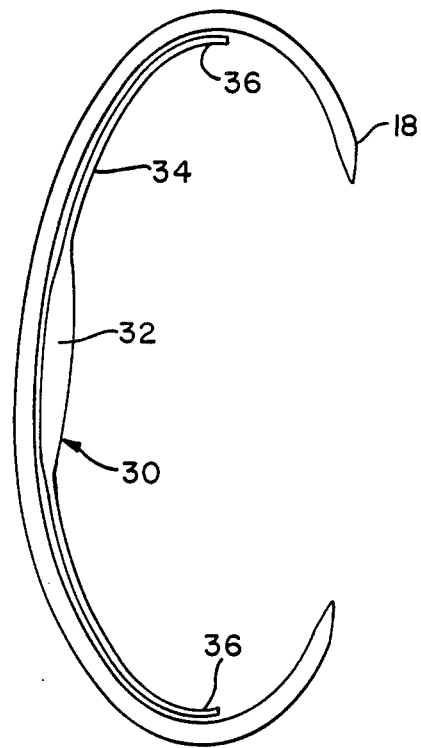
FIG. 3 is a partially schematic enlarged sectional view of a lens in accordance with the present invention within the posterior portion of the natural lens capsule.

When in position within the eye, the intraocular lens of the present invention is substantially as shown in FIGS. 2 and 3. The posterior capsule 20 and a portion of the anterior capsule 18 of the natural lens remain in the eye and the curve of the intraocular lens 30 is positioned against the concave curve of the posterior capsule 20. It is placed through the iris 14 by rolling the opposite sides of the thin, dish-shaped supporting portion 34 of the lens 30 over each other, thereby reducing the dimension of the lens and permitting it to be easily passed through a small slit (e.g., about 5 mm) in the anterior capsule. Once within the capsule, the rolled portions 34 of the intraocular lens 30 are allowed to unfold and the lens is positioned against the posterior capsule. The overall diameter of the lens 30 is approximately the same as the overall diameter of the natural lens capsule such that the lens 30 is properly positioned in correct axial alignment within the eye. Since the dish-shaped supporting portion 34 of the lens 30 is soft, due to the material of which it is made and/or because it is quite thin, the lens is supported in the eye in an extremely gentle manner. In contrast with the small supporting surfaces in intraocular lenses which use conventional haptic devices, the lens of the present invention is supported around its entire posterior surface and completely around its very soft, flexible perimeter. This perimeter edge is approximately 30 mm for a device of 9.5 mm outside diameter. This characteristic of the lens 30 substantially reduces, if not completely eliminates, the relatively high pressure associated with prior intraocular lenses.

The foregoing describes presently preferred illustrative embodiment of the present invention. It is contemplated that variations from the details described above can and will be made without departing from the spirit and scope of the invention. Accordingly, the following claims should be interpreted broadly consistent with the scope and breadth of this invention.

What I claim is:

1. An intraocular lens for implant into the posterior lens capsule of a human eye after the nucleus thereof has been removed comprising a central optical portion of biconvex configuration formed of PMMA and a relatively soft and relatively thin annular supporting portion formed of a different material surround said optical portion, said supporting portion being connected to said optical portion around its periphery and extending outwardly in a dish-shaped configuration compatible with, conforming to and shaped to lie against the posterior of the lens capsule of the human eye, the periphery of said supporting portion having a rounded shape for engagement with the inner surface of the outer periphery of the human eye lens capsule.

2. An intraocular lens in accordance with claim 1, wherein said optical portion has a diameter in the range of 3 mm to 7 mm.

3. An intraocular lens in accordance with claim 1, wherein said optical portion has a diameter of about 4.5 mm.

4. An intraocular lens in accordance with claim 2, wherein said supporting portion has an external diameter in the range of 9 mm to 14 mm.

5. An intraocular lens in accordance with claim 3, wherein said supporting portion has an external diameter of about 9.5 mm.

6. An intraocular lens in accordance with claim 1, wherein said supporting portion is shaped to provide corrective optical properties.

7. An intraocular lens in accordance with claim 1, wherein the surface of said lens facing the lens capsule posterior is non-spherically convex.

8. An intraocular lens for implant into the posterior capsule of a human eye comprising a central optical portion of biconvex configuration formed of PMMA and having a diameter in the range of about 3 mm to 7 mm, and a relatively soft and relatively thin annular supporting portion surrounding said optical portion and secured thereto, said supporting portion being formed of a different material stable in the human eye selected from the group consisting of silicone and a hydrogel, said supporting portion being connected to said optical portion completely around its periphery and extending outwardly in a dish-shaped configuration to conform to said optical portion completely the lens capsule of the human eye after the nucleus thereof has been removed, said supporting portion having a diameter in the range of 9 mm to 14 mm and a rounded supporting periphery for engagement with the inner surface of the outer periphery of the human eye lens capsule.

9. An intraocular lens in accordance with claim 8, wherein said supporting portion is shaped to selectively refract light passing therethrough to provide optically corrective properties.

10. An intraocular lens in accordance with claim 8, wherein the surface of said lens facing the lens capsule posterior is non-spherically convex.

* * * * *